US008805702B1

(12) United States Patent
Daniel

(10) Patent No.: US 8,805,702 B1
(45) Date of Patent: Aug. 12, 2014

(54) INTERACTIVE MEDICAL CARD AND METHOD OF PROCESSING MEDICAL INFORMATION STORED THEREON

(71) Applicant: Isaac S. Daniel, Miramar, FL (US)

(72) Inventor: Isaac S. Daniel, Miramar, FL (US)

( * ) Notice: Subject to any disclaimer, the term of this patent is extended or adjusted under 35 U.S.C. 154(b) by 0 days.

(21) Appl. No.: 13/959,627

(22) Filed: Aug. 5, 2013

Related U.S. Application Data

(63) Continuation of application No. 12/693,050, filed on Jan. 25, 2010, now abandoned.

(51) Int. Cl.
*G06Q 10/00* (2012.01)
*G06Q 50/00* (2012.01)
*G06F 21/31* (2013.01)
*G07F 7/08* (2006.01)

(52) U.S. Cl.
USPC ......... 705/2; 705/3; 726/2; 235/380; 235/382

(58) Field of Classification Search
USPC ................. 705/2–3; 726/2; 235/380, 382
See application file for complete search history.

(56) References Cited

U.S. PATENT DOCUMENTS

| | | | |
|---|---|---|---|
| 2005/0192844 A1* | 9/2005 | Esler et al. | 705/3 |
| 2006/0219776 A1* | 10/2006 | Finn | 235/380 |
| 2010/0071031 A1* | 3/2010 | Carter et al. | 726/2 |

\* cited by examiner

*Primary Examiner* — Joseph Burgess
(74) *Attorney, Agent, or Firm* — Carol N. Green, Esq.

(57) ABSTRACT

The present disclosure relates generally to an apparatus, system and method, and more specifically to a portable electronic interactive medical card, which includes a cardholder's medical information for which access is authenticated by biometric verification means, and more particularly to an IMC, which includes an electronic data card configured for storing thereon a biometric identifier used for releasing a detachable prescription element.

22 Claims, 9 Drawing Sheets

Name: John Doe — 202
Birthday: 1/7/60 — 204

Social Security #: 123-45-6789 — 206
Address: 1 Main Street, Anywhere, USA — 208

200

| Prescription Date | Physician's Registration # | Physician's History | Physician's E-Signature | Date Filled | Pharmacy Number | Pharmacist's Number |
|---|---|---|---|---|---|---|
| 1/2/10 | 333777 | Zithromax Z-Pack 3-Day Dose Pack | / Dr. Joseph / | | | |
| 12/17/09 | 712170 | Oxycontin - 80 mg. 30 - 1 Tablet Every 12 hours | / Dr. Dean / | 12/18/09 | 11223 | BB002 |
| 12/14/09 | 111100 | Oxycontin - 40 mg. 10 - 1 Tablet Every 12 hours | / Dr. Aain / | 12/14/09 | 10001 | CC001 |

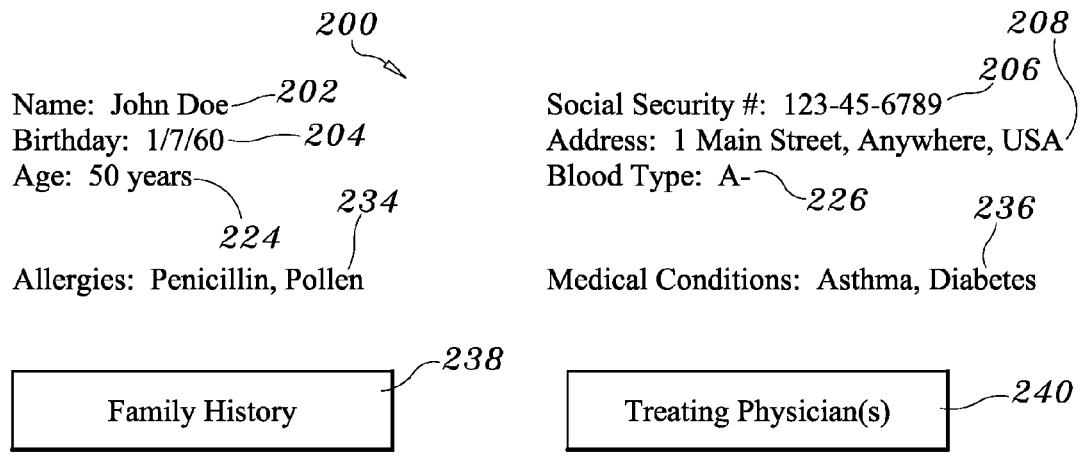

Name: John Doe —202
Birthday: 1/7/60 —204
Age: 50 years
224
Allergies: Penicillin, Pollen Social Security #: 123-45-6789 —206
Address: 1 Main Street, Anywhere, USA —208
Blood Type: A- —226
234  236
Medical Conditions: Asthma, Diabetes

| Family History —238 | | Treating Physician(s) —240 |

FIG. 2B

FAMILY HISTORY —238

Mother:
• Brain Tumor - Age 68

Father (72):
• Diabetes
• Heart Disease

FIG. 2C

TREATING PHYSICIAN(S) —240

PCP:
  Dr. Adam Bent
  232 Main Circle
  Any City, USA
  Telephone: (333) 123-4567
  Fax: (333) 123-4568

Orthopedist:
  Dr. D. Dean
  100 Fairview Terrace
  Any City, USA
  Telephone: (334) 103-4068
  Fax: (334) 103-4069

FIG. 2D

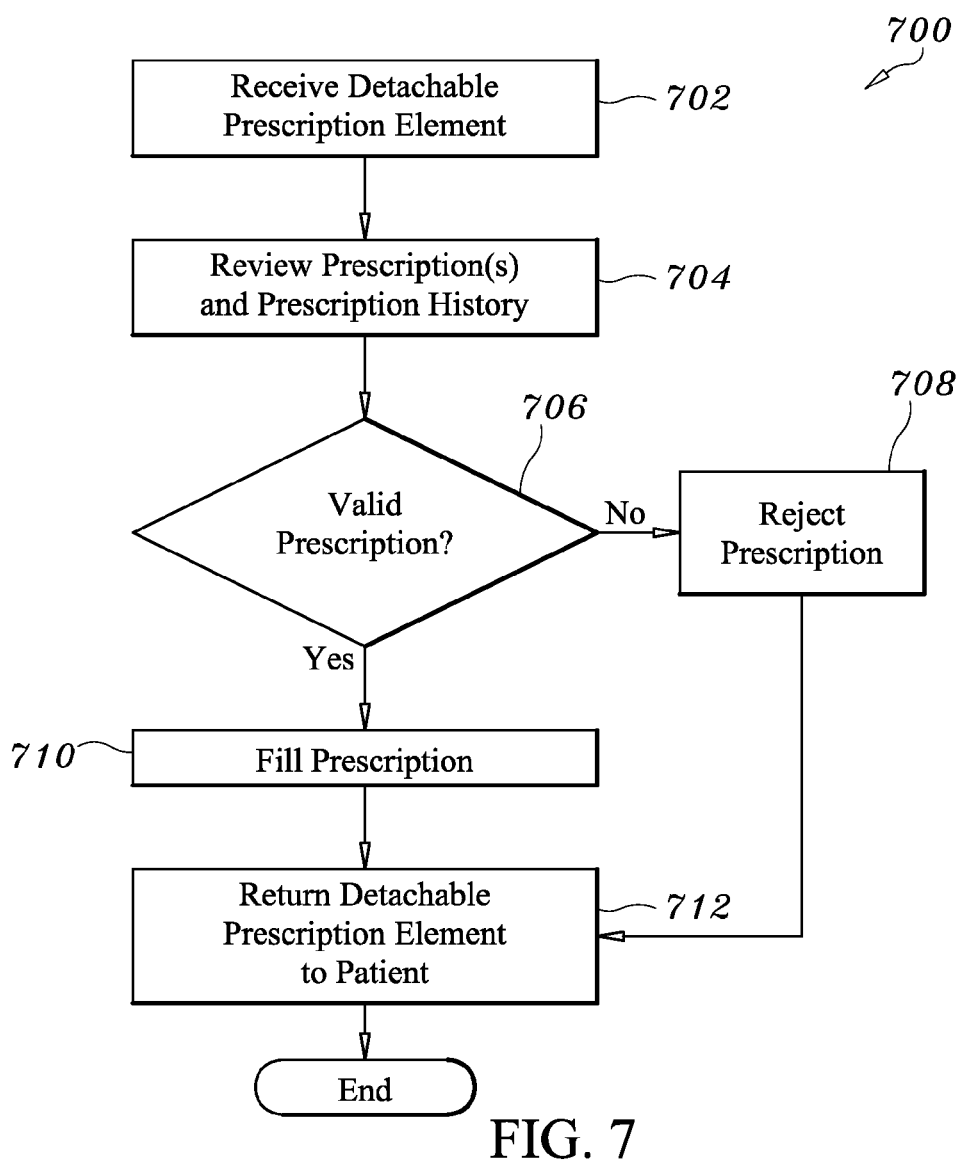

# US 8,805,702 B1

INTERACTIVE MEDICAL CARD AND METHOD OF PROCESSING MEDICAL INFORMATION STORED THEREON

PRIORITY CLAIM

This patent application is a Continuation-In-Part of, and claims priority to: United States Non-Provisional patent application Ser. No. 12/693,050 titled "An Interactive Medical Card And Method Of Processing Medical Information Stored Thereon" filed Jan. 25, 2012. The entire disclosure of the afore-mentioned patent application is incorporated by reference as if fully stated herein.

FIELD OF THE INVENTION

The present disclosure relates generally to an apparatus, system and method, and more specifically to a portable electronic interactive medical card, which includes a cardholder's medical information for which access is authenticated by biometric verification means.

BACKGROUND OF THE INVENTION

Medical emergencies generally occur with little warning and even less preparation. Under the best of circumstances a patient is conscious, alert and well able to provide his/her medical information. In reality, many patients are unconscious or so physically impaired that he or she is unable to provide such basic information as name, age, complaints, allergies and/or other relevant medical history, all of which will impact his/her treatment. Medical identification ("medical id") bracelets have been popularized as a solution for providing an alert to emergency medical professionals of known medical conditions, e.g. diabetes, asthma, etc. These medical id bracelets are limited in the amount of information that is displayed thereon. Other contributing factors, e.g. knowledge of the patient's current list of medication(s) may be relevant to treatment but not readily available. This lack of knowledge can compromise the patient's treatment. Thus, there is a need for an apparatus, system and method for providing a patient's medical information in a simple, convenient and accessible manner without compromising the confidentiality of the same.

Similar issues exist with regards to filling prescriptions where lack of information can compromise a patient's treatment. As such, patients are advised to fill all their prescriptions at the same pharmacy or at least a pharmacy within the same pharmacy chain so that there is continuity of treatment and access to a patient's prescription history. In this manner, a pharmacist or prescription software program can detect drug interactions, or abuses of controlled medications and the like. Except convenience, availability and prices are generally the controlling factors in a patient's choice of pharmacies. This places the pharmacist filling the most current prescription at a disadvantage as he/she may have incomplete information as to prior medications and/or any potentially adverse drug interactions. Pharmacists cannot rely on patient's memories as patients forget or have difficulty pronouncing and/or spelling their name of the medication(s) and may opt to take an educated guess which is unreliable for its lack of precision. Therefore, it would be helpful for a patient's current list of medications, i.e. prescription history, to be portable and available to any registered pharmacist for reference and review on an as needed basis.

Accordingly, the various embodiments and disclosures described herein satisfies these long felt needs and solves the limitations of the prior art in a new and novel manner.

SUMMARY OF THE INVENTION

An objective of the apparatus, system and method disclosed herein is to provide a convenient interactive medical card ("IMC") that includes biometric verification means positioned thereon for receiving and storing a biometric identifier used as a unique identifier of the card holder.

Another objective of the apparatus, system and method disclosed herein is to provide an IMC configured for storing thereon a biometric identifier used for releasing a detachable prescription element.

Yet another objective of the apparatus, system and method disclosed herein is to provide for the electronic storage of a patient's medical information including the patient's prescription history.

Still yet another objective of the apparatus, system and method disclosed herein is to provide an IMC that contains a patient's confidential medical information readily accessible to authorized personnel while maintaining the privacy and confidentiality of the same.

The present disclosure relates generally to an apparatus, system and method, and more particularly to an IMC, which includes an electronic data card configured for storing thereon a biometric identifier used for releasing a detachable prescription element. The detachable prescription element includes at least one flash memory card. "Biometric identifier" as used herein describes a valid biometric sample obtained from a card holder via the biometric verification means, and stored on the IMC for later reference. Biometric verification means includes but is not limited to: fingerprint recognition means, hand geometry recognition means, palm geometry recognition means, iris recognition means, retina recognition means, speech recognition means and any other biometric verification means that are known and used in the arts. Biometric verification means may include at least one processor disposed in communication with, for example, a fingerprint scanner, hand geometry scanner, a palm geometry scanner, iris scanner, retina scanner, or a user interface which includes an audio receiving circuit capable of receiving audio signals at predetermined frequencies and/or with additional hardware complete with electronic circuitry.

IMC is selected from the group of electronic devices consisting essentially of smart cards, memory cards, and processor cards, with at least one memory means embedded therein for storing a patient's biometric identifier and/or medical information. Medical information includes but is not limited to a patient's: name, birthday, social security number, address, prescription date, prescribing physician registration number, prescription history, prescribing physician's electronic signature, date prescription filled, pharmacy's registration number, pharmacist's license number, age, blood type, sex, race, marital status, allergies, known medical conditions, family history, a treating physician's contact information, color of eyes, height, primary care physician's name, primary care physician's address, primary care physician's contact information, insurance provider's name, insurer's address, insurer's telephone number, medical history and the like.

IMC includes at least one processor positioned within configured for performing any one or more of the following: validating a biometric sample with a biometric identifier stored thereon; releasing the detachable prescription element; and communicating with a computer via an application program. IMC also includes biometric identifier or medical information stored within IMC's at least one memory means. The at least one memory means may comprise of storage hardware.

IMC is a functional component of a system, where the system comprises of: a computer; an application program executable on the computer; and the IMC which includes an electronic data card configured for storing thereon, a patient's medical information accessible by the application program, as well as a biometric identifier used for releasing a detachable prescription element. System also comprises of biometric verification means positioned on the interactive medical card, where the biometric verification means is configured for receiving at least one biometric sample, which is compared to the biometric identifier stored thereon as a means of authenticating the IMC card holder.

The IMC of the system includes at least one processor configured for performing any one or more of the following: validating a biometric sample with a biometric identifier stored thereon; releasing the detachable prescription element; and communicating with the computer via an application program. System may include software components, which may comprise of the computer; and the application program executable on the computer configured for: establishing access to the patient's medical information stored on an IMC; retrieving patient's medical information from the IMC; storing patient's medical information received from a medical care provider on the IMC; or the computer, or a combination of the computer and the IMC; validating authorized access to the patient's medical information by the medical care provider; detecting a presence of at least one medical information field, or fields, adapted for receiving patient medical information; and automatically propagating the field or fields with patient's medical information.

In some embodiments, method comprises of: providing an interactive medical card, which includes an electronic data card configured for storing thereon a patient's medical information as well as a biometric identifier used for releasing a detachable prescription element. Method also comprises of providing biometric verification means positioned on the IMC, where biometric verification means include the verification means as described above. In some embodiments, method comprises of providing at least one processor positioned within the IMC configured for performing any one or more of the following: validating a biometric sample with a biometric identifier; releasing the detachable prescription element; and communicating with a computer via an application program as well as reading any one or more of the following: a biometric sample, biometric identifier stored on the interactive medical card or medical information; releasing the detachable prescription element; and communicating with a computer via an application program.

In some embodiments method comprises of: providing a computer; and providing an application program executable on the computer configured for: establishing access to the patient's medical information stored on an IMC; retrieving patient's medical information from the IMC; storing patient's medical information received from a medical care provider on IMC; or the computer, or a combination of the computer and the IMC; validating authorized access to the patient's medical information by the medical care provider; detecting a presence of at least one medical information field, or fields, adapted for receiving patient medical information; and automatically propagating the field or fields with patient's medical information.

Additional objectives of the present invention will appear as the description proceeds.

The foregoing and other objects and advantages will appear from the description to follow. In the description, references are made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views. The following detailed description is, therefore, not to be taken in a limiting sense, and the scope of the present invention is best defined by the appended claims.

BRIEF DESCRIPTION OF THE DRAWINGS

Further objectives and advantages of the system and method may be derived by referring to the detailed description and claims when considered in connection with the Figures, wherein like reference numbers refer to similar items throughout the Figures.

FIG. 2A shows exemplary medical information that may be stored on the IMC.

FIG. 2B shows exemplary medical information that may be stored on the IMC according to an embodiment.

FIG. 2C shows exemplary medical information that may be stored on the IMC according to an embodiment, e.g. the patient's medical family history.

FIG. 2D shows exemplary medical information that may be stored on the IMC according to an embodiment, e.g. the treating physician's contact information.

FIG. 6 is a sample flowchart of a block diagram of an exemplary method according to an embodiment.

FIG. 7 is a sample flowchart of a block diagram of an exemplary method of processing a patient's prescription using the detachable prescription element according to an embodiment.

DETAILED DESCRIPTION OF THE PREFERRED EMBODIMENT

Figure 1A:
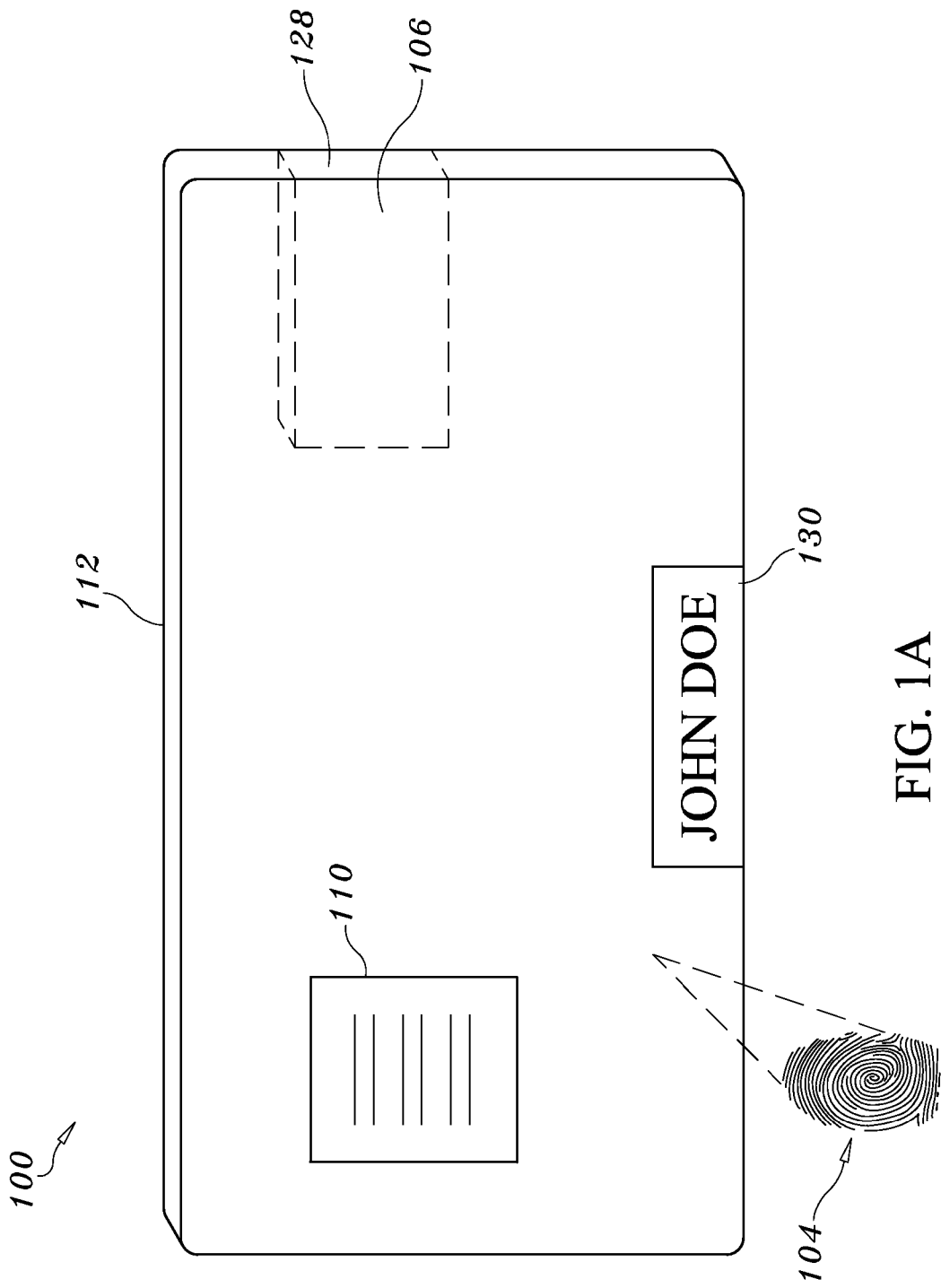
FIG. 1A is an exemplary embodiment of the IMC.

The following discussion describes in detail, varied embodiments of the system and methods disclosed herein. However, this discussion should not be construed, as limiting the invention to those particular embodiments, as practitioners skilled in the art will appreciate that an apparatus or system may vary as to configuration and as to details of the parts, and that a method may vary as to the specific steps and sequence, without departing from the basic concepts as disclosed herein. Similarly, the elements described herein may be implemented separately, or in various combinations without departing from the teachings of the present invention.

Turning now descriptively to the drawings, in which similar reference characters denote similar elements throughout the several views.

*Apparatus & Systems*

Figure 1B:
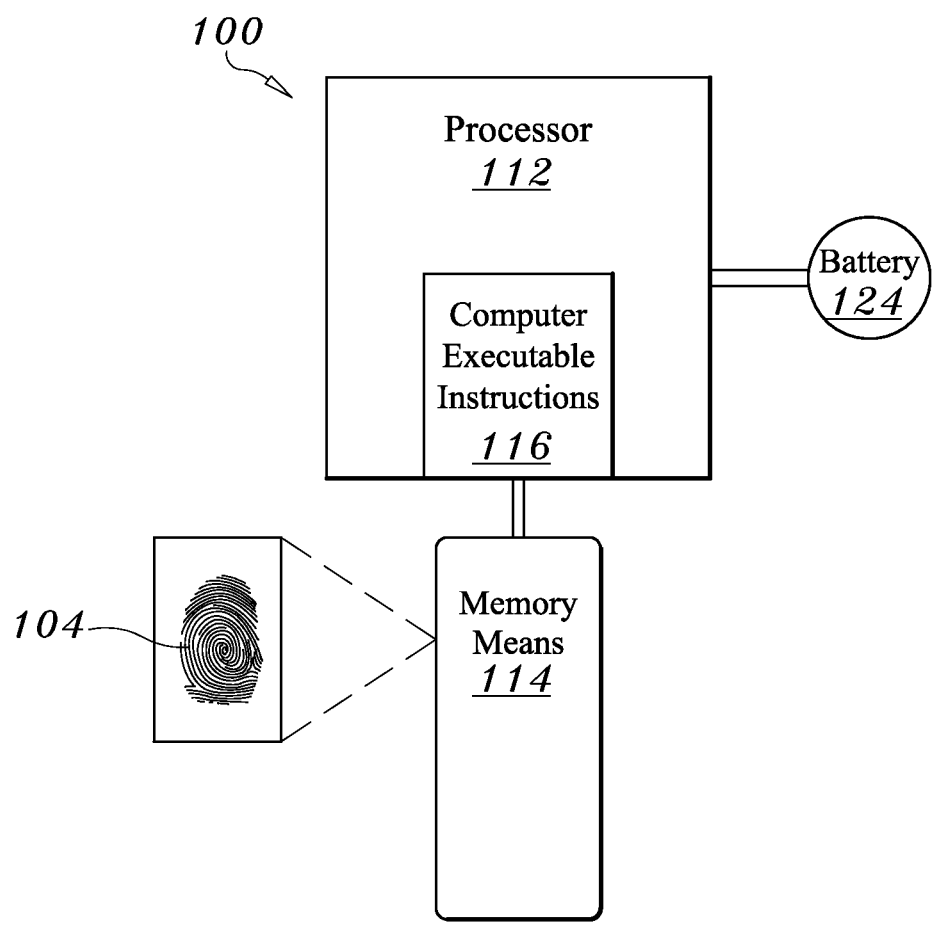
FIG. 1B is an exemplary embodiment of the IMC.

FIGS. 1A & 1B are exemplary embodiments of the IMC 100. IMC 100 is an electronic data card dimensioned in size similar to credit cards as are well known and used in the arts. IMC 100 is configured for storing thereon a biometric identifier 104 used for releasing a detachable prescription element 106. "Biometric identifier" 104 as used herein describes a biometric sample 108 obtained from a card holder via the biometric verification means 110 positioned on the IMC 100, and stored thereon for future reference and comparison. Biometric identifier 104 uniquely identifies the individual based on his/her intrinsic physical traits, e.g. fingerprints, retina scan, palm geometry, hand geometry, speech, and or other biometric identifiers 104 that are used in the arts.

Biometric verification means 110 includes but is not limited to: fingerprint recognition means, hand geometry recognition means, palm geometry recognition means, iris recognition means, retina recognition means, speech recognition means and any other biometric verification means 110 that are known and used in the arts. Biometric verification means 110 may include at least one processor 112 disposed in electronic communication with, for example, a fingerprint scanner, hand geometry scanner, a palm geometry scanner, iris scanner, retina scanner, or a user interface which includes an audio receiving circuit capable of receiving audio signals at predetermined frequencies and/or with additional hardware complete with electronic circuitry. Illustratively, as seen in FIG. 1A, the biometric verification means 110 includes a fingerprint scanner, where the processor 112 controls the functionality of the fingerprint scanner, generates the varied algorithms for storage of the first valid biometric sample 108 as a biometric identifier 104 and validates the images of other biometric samples 108, 108' subsequently received from the card holder with the biometric identifier 104 stored thereon.

IMC 100 is selected from the group of electronic devices consisting essentially of programmable smart cards, memory cards, and processor cards, with at least one memory means 114 embedded therein configured for storing thereon a biometric identifier 104 and/or a patient's medical information. Medical information 200 (as shown in FIG. 2A) includes but is not limited to name, birthday, social security number, address, prescription date, prescribing physician registration number, prescription history, prescribing physician's electronic signature, date prescription filled, pharmacy's registration number, pharmacist's license number, age, blood type, sex, race, marital status, allergies, known medical conditions, family history, a treating physician's contact information, color of eyes, height, primary care physician's name, primary care physician's address, primary care physician's contact information, insurance provider's name, insurer's address, insurer's telephone number, medical history and the like.

The IMC 100 comprises of computer executable instructions 116 readable by the at least one processor 112 and operative to perform the varied system functions disclosed herein. The computer executable instructions 116 may be any type of computer executable instructions, which may be in the form of a computer program, the program being composed in any suitable programming language or source code, such as C++, C, JAVA, JavaScript, HTML, XML, and other programming languages. The computer executable instructions 116 may be loaded directly on the at least one processor 112 positioned within the IMC 100 and is configured for performing any one or more of the following: validating a biometric sample 108 with a biometric identifier 104 stored on the IMC's at least one memory means 114; releasing the detachable prescription element 106; and communicating with a computer 302 (as shown in FIG. 3) via an application program 118.

Figure 3:
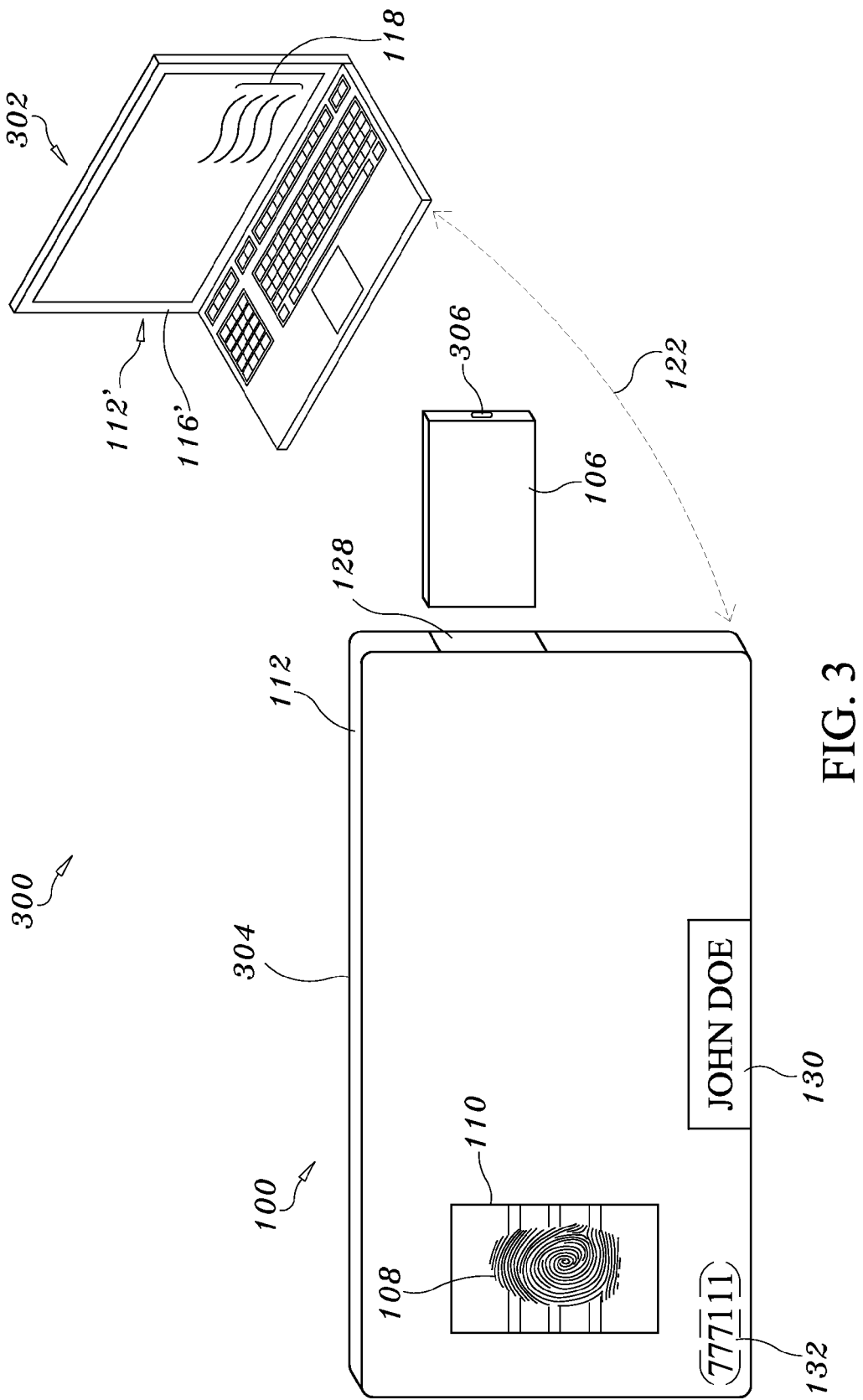
FIG. 3 shows an exemplary system according to one embodiment.

The detachable prescription element 106 as exemplified herein may be adapted with electrical contacts 120, e.g. a USB connection, for establishing wired and/or wireless connectivity to the IMC 100 and/or the computer 302 (as shown in FIG. 3). Alternatively, a wireless connection may be established, wherein communication access is established in response to the IMC's proximity to a client server computer 302 that is enabled with the application program 118 and upon validation by the biometric verification means 110 of biometric samples 108, 108' subsequently received from the IMC holder matching the biometric identifier 104 stored thereon. In this manner, the detachable prescription element 106 is not released unless the IMC 100 is within a certain predetermined proximity 122 to the server computer 302. In this manner, a secondary level of authentication is required for detachable prescription element 106 to be released and the medical care providers can authenticate the identity of the individual being treated for medical services, including but not limited to pharmaceutical services, general medical or emergency medical care services. The predetermined proximity 122 may be programmed for distances that the administrator of the application program considered reasonable, e.g. a radius of 5, 10 or 15 miles with the greater distances for more remote locations.

Processor 112 may be any type of processor, such as, but not limited to, a central processing unit (CPU), a microprocessor, a video processor, a front end processor, a coprocessor, a single-core processor, a multi-core processor, and the like.

The at least one memory means 114 exemplified in FIG. 1B may include a hardware component, e.g. storage hardware, in electrical communication with at least one processor 112. Storage hardware may include, but is not limited to, read-only memory, such as CD-ROMs, DVDs, floppy disks, and the like, read and write memory, such as a hard drive, floppy disc, CD-RW, DVD-RW, solid state memory, such as solid state hard drives, flash cards, memory chips, and the like, and random access memory. In one embodiment, the at least one memory means 114 may comprise of both hardware and software components. In some embodiments, at least one memory means 114 may be embedded within at least one processor 112 where the information stored therein is encrypted for privacy purposes. In other embodiments, the at least one memory means 114 is the detachable prescription element 106, which includes at least one flash memory card adapted with electrical contacts for establishing wired and/or wireless connectivity to a computer.

In one embodiment, the IMC holder's biometric identifier 104 is stored within the at least one memory means 114 embedded within the smart card processor 112 while the medical information is stored on the IMC's detachable prescription element 106. In another embodiment, both IMC holder's biometric identifier 104 and the patient's medical information are stored within the IMC's at least one memory means 114 embedded within the smart card processor 112". In still yet another embodiment, both the biometric identifier 104 and medical information are stored on the IMC's detachable prescription element 106.

IMC 100 may optionally include a battery 124, which serves as a power source for the at least one processor 112 positioned therein. In one embodiment, IMC 100 is adapted with electrical contacts for establishing wired and/or wireless connectivity to a charger, e.g. a docking station, and as such may not include a battery 124. In that event, processor 112 detects when the IMC 100 has been disconnected from an external power source and switches apparatus 100's power source to an internal power source, such as the battery 124.

Figure 1C:
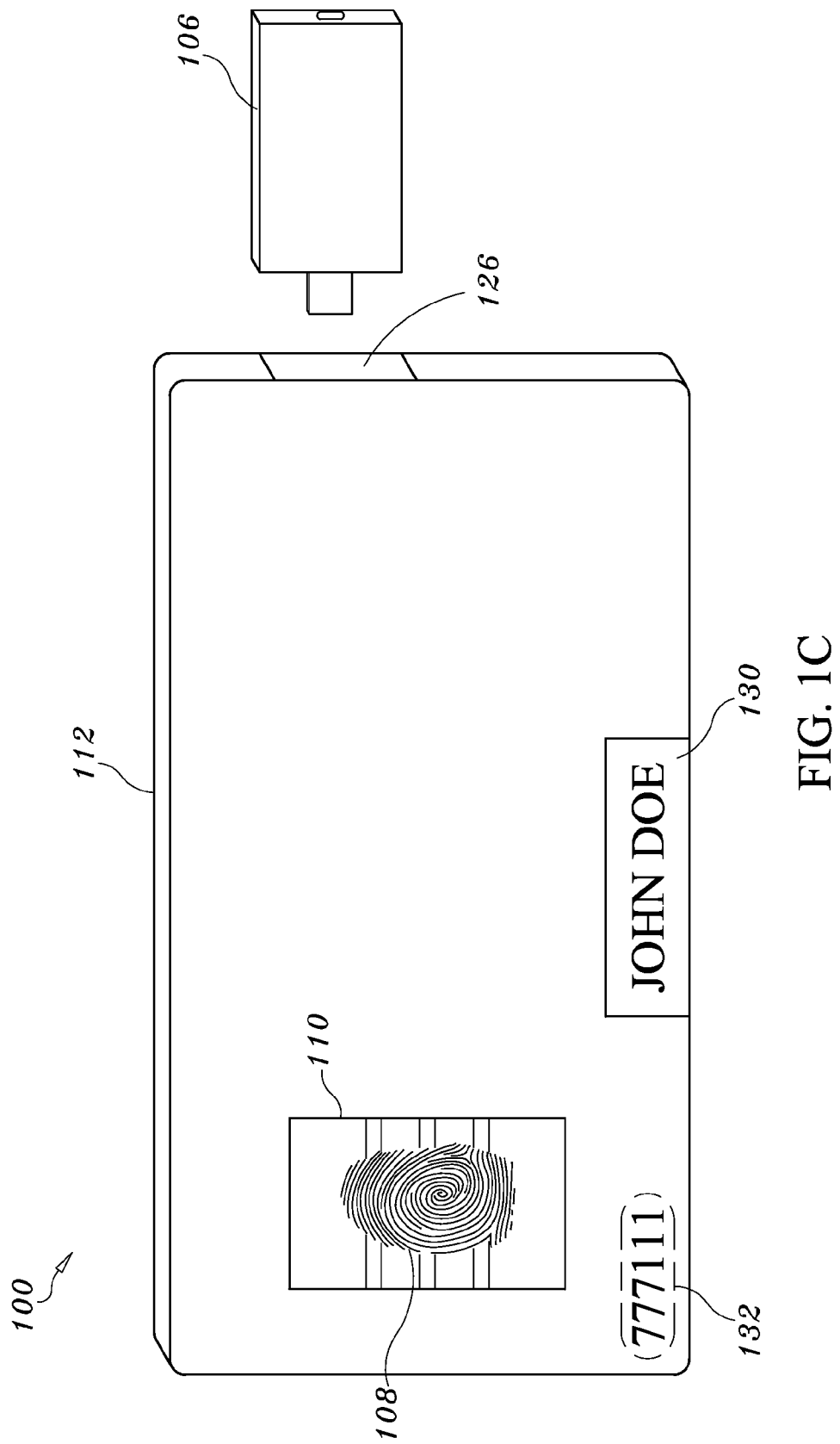
FIG. 1C is an exemplary embodiment of the IMC with the detachable prescription element released from the IMC.

FIG. 1C is an exemplary embodiment of the IMC 100 with the detachable prescription element 106 released from the IMC 100. Releasing the detachable prescription element 106 requires the IMC holder to submit a valid biometric sample 108 that is compared to the biometric identifier 104 stored thereon for an identical match. For example, in the instance where the biometric verification means 110 includes a fingerprint scanner, the IMC holder will be required to submit a biometric sample 108 using the same finger previously used to obtain the original biometric sample 108 stored thereon as the biometric identifier 108. If the biometric sample 108 is an identical match to the biometric identifier 108, processor 112 which is disposed in communication with the fingerprint scanner, initiates the release of the detachable prescription element 106 to release it from the IMC 100 if additionally, the IMC 100 is within a predetermined proximity 122 to a client server computer 302. If so, processor 112 initiates the release by activating a release and retain mechanism 126 located within the IMC 100, e.g. a spring assembly, a release button or the like, that securely retains the detachable prescription element 106 within the IMC 100 until it is released by the validation of the biometric sample 108 and the IMC 100 being within the predetermined proximity 122. Once released, the detachable prescription element 106 is ejected through an aperture 128 on the IMC 100, which is sized and configured to allow the detachable prescription element 106 to be ejected therefrom.

IMC 100 may also include other indicia of identification, e.g. a name plate 130, which may be used to identify the card holder's name and or address that is printed thereon. In some embodiments, IMC 100 is assigned a unique identification number 132, e.g. a serial number used to track ownership and/or warranty purposes. The unique identifying number 132 may be assigned via a random number generating program, comprising of numerals, characters, alphanumeric characters or any other unique identifiers that are known and used in the arts.

FIG. 2A-2D show exemplary medical information 200 that may be stored on the IMC 100. Medical information 200 may include but is not limited to name 202, birthday 204, social security number 206, address 208, prescription date 210, prescribing physician registration number 212, prescription history 214, prescribing physician's electronic signature 216, date prescription filled 218, pharmacy's registration number 220, pharmacist's license number 222, age 224, blood type 226, sex 228 (not shown), race 230 (not shown), marital status 232 (not shown), allergies 234, known medical conditions 236, family history 238, a treating physician's contact information 240, color of eyes 242 (not shown), height 244 (not shown), primary care physician's name 246 (not shown), primary care physician's address 248 (not shown), primary care physician's contact information 250 (not shown), insurance provider's name 252 (not shown), address 254 (not shown), telephone number 256 (not shown), medical history 258 (not shown) and the like.

In some embodiments, medical information 200 is readily accessible to a health care provider without additional security controls after the detachable prescription element 106 has been detached from the IMC 100. In other embodiments, additional security controls may be required to access the medical information, e.g. providing a valid physician's registration number 220 to an application program 118 to authorize the physician or pharmacist's access to the medical information 200 or prescription information stored thereon. In the preferred embodiment, the medical information 200 is readily accessible to emergency care providers without any further security controls, such that the patient's medical information is readily accessible and available.

In some embodiments, certain medical information 200 is populated onto the detachable prescription element 106 via an application program 118. For example, when a pharmacist has completed the process of filling the prescription, the application program 118 detects the presence of at least one medical information 100 field, or fields, that is adapted for receiving patient medical information 200 and automatically propagates the field or fields with patient's medical information 200, e.g. date filled 218, pharmacy number 220 and/or the pharmacists' license number 222. In some embodiments, such information is manually inputted and stored on the detachable prescription element 106, which is returned to the patient.

FIG. 2B shows exemplary medical information 200 that may be stored on the IMC 100 according to an embodiment. Treating physicians may use the IMC's detachable prescription element 106 to update and store the patient's family history 238, the treating physician's contact information 240 as well as a new prescription to be filled and/or any other relevant medical information 200, e.g. allergies 234, medical conditions 236 and the like. Since the IMC 100 remains in the patient's possession, a thorough family history 238 that is obtained and stored thereon, makes the IMC 100 an invaluable portable concise documentation of the patient's medical information 200 available to all treating physicians regardless of where the patient is located in the world.

FIG. 2C shows exemplary medical information 200 that may be stored on the IMC 100 according to an embodiment, e.g. the patient's medical family history 238, which can be an important predictor of genetic diseases as well as identifying the patient's risks of developing other health conditions. The patient's family history 238 may not be readily viewable to a treating physician as it may require the treating physician to toggle through certain software application menus via a user interface to view and/or store the same. In this manner, the patient's family history 238 is accessible on an as needed basis but not readily viewable to other personnel, e.g. pharmacists, to whom the information is of no concern.

FIG. 2D shows exemplary medical information 200 that may be stored on the IMC 100 according to an embodiment, e.g. the treating physician's contact information 240. The treating physician's contact information 240 is made available such that interested medical care providers have access to the information, e.g. another doctor may need clarifying information or reports of certain medical procedures performed at the direction of another specialist. Here too, the treating physician's contact information 240 may not be readily viewable and may require the medical care provider to toggle through certain software application menus via a user interface to view and/or store the same.

FIG. 3 shows an exemplary system 300 according to one embodiment. System 300 comprises of a client server computer 302 enabled with an application program 118 comprising of computer executable instructions 116' executable on the computer 302; and the interactive medical card 100 that is an electronic data card 102 configured for storing thereon a patient's medical information 200; biometric verification means 110 positioned on the IMC 100 wherein the biometric verification means 110 is in electrical communication with at least one processor 112 and is configured for validating a biometric sample 108 with a biometric identifier 104 stored thereon; and at least one sensor 304 positioned within the IMC 100 that is in electronic communication with the at least one processor 112 that is equipped with computer executable instructions 116, wherein the at least one sensor 304 is programmed for determining if the IMC 100 is within a predetermined proximity 122 to a client server computer 302 enabled with an application program 118, and for releasing the detachable prescription element 106 only if the biometric sample 108 is valid and the IMC 100 is within the predetermined proximity 122.

The at least one sensor 304 may be any kind of sensor, including, but not limited to, a programmable proximity sensor, a WiFi sensor, or Bluetooth sensor with electronic communication means for determining connectivity to the server computer 302. In preferred embodiments, at least one sensor 304 may include a field of sensing that is greater than or encompasses the proximity to the client server computer. As such, the IMC 100 is inoperable if it is not within the programmed predetermined proximity 122, i.e. a set radius of the client server computer 302, as it will fail to release the detachable prescription element 106 even if the biometric sample 108 submitted matches the biometric identifier 104 stored thereon.

Computer 302, e.g. a network enabled computer, a laptop or personal digital assistant subject to wired/wireless connectivity is configured with an application program 118 to allow communications between the computer 302 and the medical information 200 that may be stored on the detachable prescription element 106 on the IMC 100. Medical information 200 includes the medical information 200 previously described herein and the like. The application program 118 may comprise in part of a browser, such as for use on a personal computer 302 and/or a user interface.

Computer 302 includes a processor 112' configured with computer executable instruction code 116' executable by the computer processor 112'. IMC 100 also comprises of computer executable instruction code 116 readable by its at least one processor 112' and operative to perform the varied system functions of the IMC 100. The computer executable instruction code 116' may be any type of computer executable instruction code 116, which may be in the form of a computer program, the program being composed in any suitable programming language or source code, such as C++, C, JAVA, JavaScript, HTML, XML, and other programming languages. The computer executable instruction code 116' may be loaded directly on the processor 112', or may be stored in the computer's memory means 114' (not shown), such as, but not limited to, computer readable media, such as, but not limited to, a hard drive, a solid state drive, a flash memory, random access memory, CD-ROM, CD-R, CD-RW, DVD-ROM, DVD-R, DVD-RW, and the like.

IMC 100 also includes a processor 112, where the IMC processor 112 and/or the computer processor 112' may be any type of processors 112, 112' such as a central processing unit (CPU), a processor 112, a front end processor, a coprocessor, a single-core processor, a multi-core processor, as well as any known processor 112 that's used in the arts. The IMC's processor 112 is configured for performing any one or more of the following: validating a biometric sample 108 with a biometric identifier 104 stored thereon; releasing the detachable prescription element; 106, and communicating with the computer 302 via an application program 118.

System 300 also comprises of biometric verification means 102 positioned on the IMC 100, where the biometric verification means 110 is configured for receiving at least one biometric sample 104, which is compared with a biometric identifier 104 stored thereon. Biometric verification means 110 includes but is not limited to: fingerprint recognition means, hand geometry recognition means, palm geometry recognition means, iris recognition means, retina recognition means, speech recognition means and any other biometric verification means 110 that are known and used in the arts. Biometric verification means 110 may include at least one processor 112 disposed in communication with, for example, a fingerprint scanner, hand geometry scanner, a palm geometry scanner, iris scanner, retina scanner, or a user interface which includes an audio receiving circuit capable of receiving audio signals at predetermined frequencies and/or with additional hardware complete with electronic circuitry as described above. When the IMC holder provides a valid biometric sample 108 the detachable prescription element 106 becomes detached and is now available for use by a medical care provider so long as the IMC 100 is within the predetermined proximity 122.

The detachable prescription element 106 includes at least one flash memory card and may be adapted with electrical contacts 306 for establishing wired and/or wireless connectivity to the computer 302. In one embodiment, the detachable prescription element 106 is the IMC's at least one memory means 114. In some embodiments, the IMC's at least one memory means 114 may be embedded within at least one processor 112 where the information stored therein is encrypted for privacy purposes. In other embodiments, the at least one memory means 114 may comprise of a hardware component, e.g. storage hardware, in electrical communication with at least one processor 112. Such storage hardware may include, but is not limited to, read-only memory, such as CD-ROMs, DVDs, floppy disks, and the like, read and write memory, such as a hard drive, floppy disc, CD-RW, DVD-RW, solid state memory, such as solid state hard drives, flash disks, and the like, and random access memory.

System 200 includes software components which may comprise of an application program 118 that resides in the IMC's processor 112 and comprises of computer executable instructions 116" executable by the IMC's processor 112. Application program 118 may comprise in part of a browser residing on the client server computer 302, where the application program 118 is configured for establishing access to the IMC 100 such that the proximity to the IMC 100 can be determined for the release of the detachable prescription element 106 if the biometric sample 108 is validated; and for providing a graphical user interface for reviewing, adding or storing information on the detachable prescription element 106; accessing patient's medical information 200 stored on the IMC 100; retrieving patient's medical information 200 from the IMC 100; storing patient's medical information 200 received from a medical care provider on the IMC 100; or the computer 302, or a combination of the computer 302 and the IMC 100; validating authorized access to the patient's medical information 200 by the medical care provider; detecting a presence of at least one medical information 200 field, or fields, adapted for receiving patient medical information 200; and automatically propagating the field or fields with patient's medical information 200.

Methods

Figure 4:
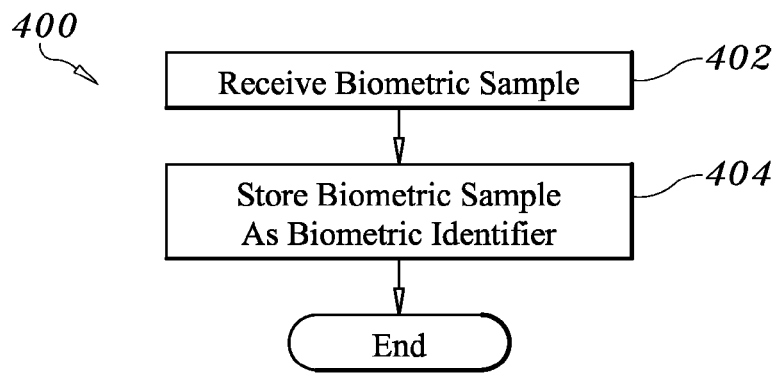
FIG. 4 is a sample flowchart of a block diagram of an exemplary method in accordance with one embodiment.

FIG. 4 is a sample flowchart of a block diagram of an exemplary method 400 of storing the patient's biometric identifier 104 in accordance with one embodiment. The method 300 comprises of processor 112 receiving a first valid biometric sample 108 (step 402) from the patient and storing the biometric sample 108 as a biometric identifier 104 (step 404) on IMC's memory means 104.

Figure 5:
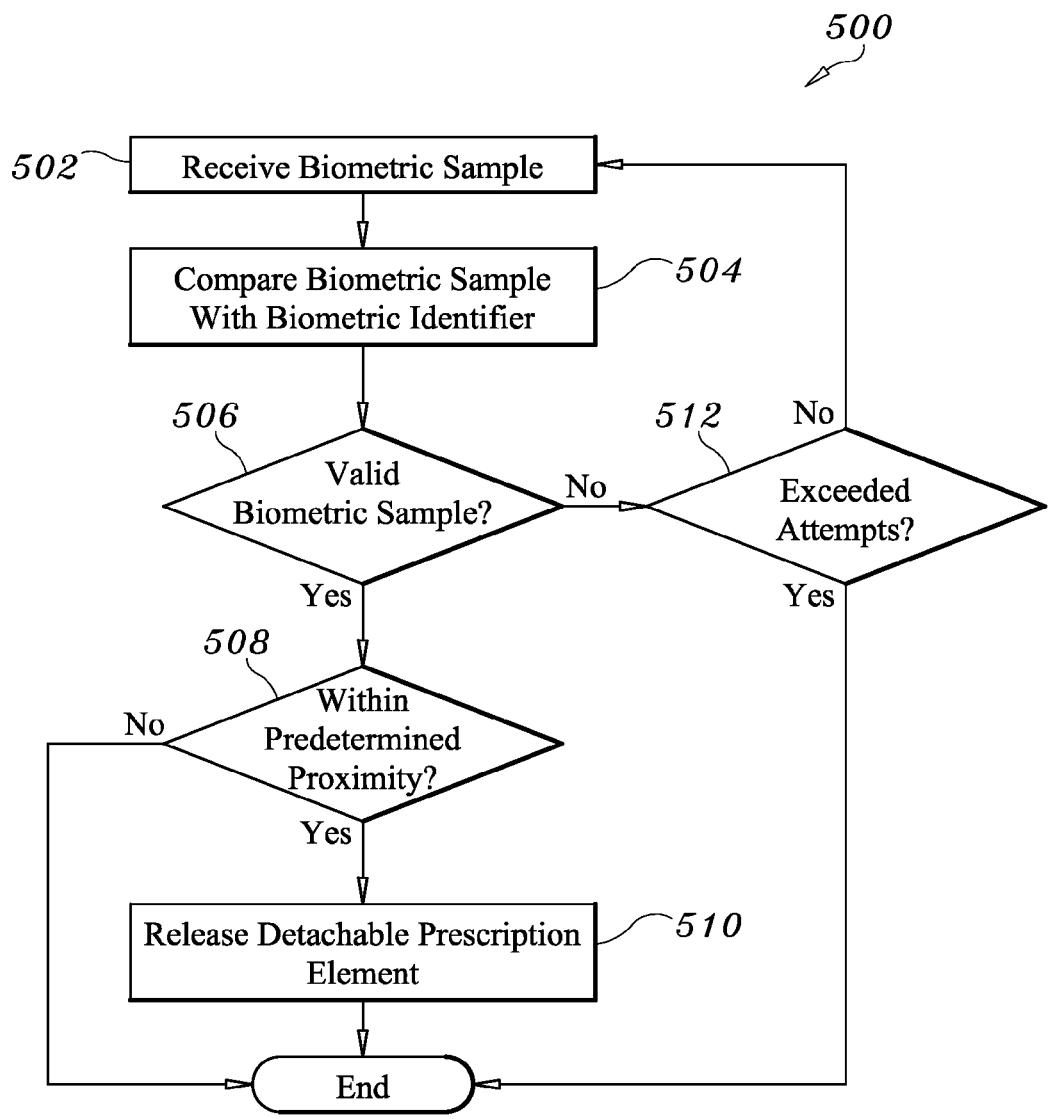
FIG. 5 is a sample flowchart of a block diagram of an exemplary method according to an embodiment.

FIG. 5 is a sample flowchart of a block diagram of an exemplary method 500 of the invention. Method 500 comprises receiving a new biometric sample 108 on the IMC 100 (step 502) from the IMC holder and comparing the new biometric sample 108 with the biometric identifier 110 (step 504) stored thereon with biometric verification means 110 positioned on the IMC 100. Method 500 further comprises determining if the biometric sample 108 is a valid (step 506), i.e. the biometric sample 108 is an identical match to the biometric identifier 110 stored thereon. If so, method 500 comprises verifying that the IMC 100 is within a predetermined proximity 122 to a client's server computer 302 enabled with an application program 118 (step 508). Only if true, method 500 comprises releasing the detachable prescription element 106 (step 510) housed within the IMC 100 by activating a spring assembly, to release the detachable prescription element 106, which will be ejected through the aperture 128. Once the detachable prescription element 106 has been released from the IMC 100 it becomes available for use by a medical care provider, e.g. a treating physician or pharmacist to access, edit or store medical information stored thereon or process the same.

If the biometric sample is invalid (step 506), i.e. failed to match the biometric identifier 104 stored thereon within the calibrated precision range for an identical match, e.g. use of the wrong finger, then IMC holder may provide an additional biometric sample 108, which is received an processed in accordance with steps 502-506 until the detachable prescription element 106 is released. In some embodiments, processor 112 may be programmed to block access to the IMC's medical information 200 if multiple, consecutive, unsuccessful attempts are made within a prescribed time period. In that embodiment, an additional verification step may be incorporated into the method 500 whereby after verifying that the biometric sample 10 is valid (step 506), processor 112 verifies if the maximum number of attempts (step 512) has been exceeded. If the maximum number of attempts has not been exceeded, method 500 will return to steps 502-506. However, if it has, processor 112 locks the medical information 200 and/or the spring assembly that controls the release of the detachable prescription element 106 and it will not be released.

FIG. 6 is a sample flowchart of a block diagram of an exemplary method 600 of storing a patient's medical information, e.g. adding a prescription, on the detachable prescription element 106 according to an embodiment. In the exemplary method 600, a treating physician may receive the detachable prescription element 106 (step 602) that has been released from the IMC 100. The physician may insert the detachable prescription element 106 which is configured with electrical contacts for connecting to a computer 302, into his or her computer 302 to access the patient's medical information 200. As such, the medical care provider may then provide the medical information, e.g. prescription, which is electronically stored thereon (step 604). In some embodiments, the doctor will need to access the patient's prescription information with additional security controls, e.g. providing a valid password that is authenticated with a registry. In other embodiments no additional security controls are necessary to access the patient's prescription information.

FIG. 7 is a sample flowchart of a block diagram of an exemplary method 700 of processing a patient's prescription using the detachable prescription element 106 according to an embodiment. A pharmacist may receive the detachable prescription element 106 (step 702) from the patient and review the patient's prescription (step 704) and/or the prescription history to determine for example, whether or not the prescription has expired, was prescribed by an authorized physician and/or contains other self authenticating information. If the prescription is valid (step 706) the pharmacist may fill the prescription (step 710) and return the detachable prescription element 106 to the patient (step 712) with for example the filled prescription. However, if the prescription is not valid (step 706), e.g. a stale prescription for controlled medication, then the pharmacist may reject the prescription (step 708) and return the detachable prescription element 106 to the patient (step 712).

Hardware and Operating Environment

This section provides an overview of example hardware and the operating environments in conjunction with which embodiments of the inventive subject matter can be implemented. A software program may be launched from a computer readable medium in a computer-based system 100 to execute the functions defined in the software program. Various programming languages may be employed to create software programs designed to implement and perform the methods disclosed herein. The programs may be structured in an object-orientated format using an object-oriented language such as Java or C++. Alternatively the programs may be structured in a procedure-oriented format using a procedural language, such as assembly or C. The software components may communicate using a number of mechanisms, such as application program interfaces, or inter-process communication techniques, including remote procedure calls. The teachings of various embodiments are not limited to any particular programming language or environment. Thus, other embodiments may be realized, as discussed regarding FIG. 8 below.

Figure 8:
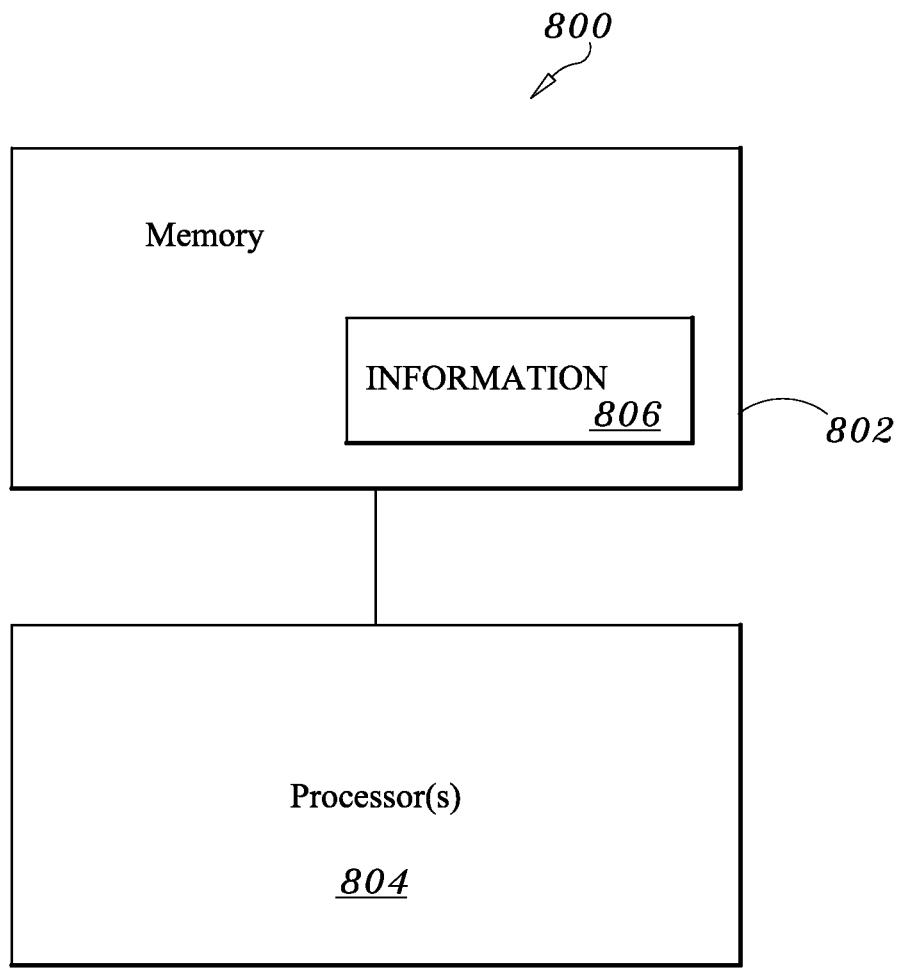
FIG. 8 is a block diagram representing an apparatus 800 according to various embodiments.

FIG. 8 is a block diagram representing an apparatus 800 according to various embodiments. Such embodiments may comprise a computer, a memory system, a magnetic or optical disk, some other storage device, or any type of electronic device or system. The apparatus 800 may include one or more processor(s) 804 coupled to a machine-accessible medium such as a memory 802 (e.g., a memory including electrical, optical, or electromagnetic elements). The medium may contain associated information 806 (e.g., computer program instructions, data, or both) which, when accessed, results in a machine (e.g., the processor(s) 804) performing the activities previously described herein.

The principles of the present disclosure may be applied to all types of computers, systems, and the like, include desktop computers, servers, notebook computers, personal digital assistants, microcomputers, and the like. However, the present disclosure may not be limited to the personal computer.

While the principles of the disclosure have been described herein, it is to be understood by those skilled in the art that this description is made only by way of example and not as a limitation as to the scope of the disclosure. Other embodiments are contemplated within the scope of the present disclosure in addition to the exemplary embodiments shown and described herein. Modifications and substitutions by one of ordinary skill in the art are considered to be within the scope of the present disclosure.

What is claimed is:

1. An apparatus comprising of:
   (a) an interactive medical card that is an electronic data card configured for storing medical information thereon;
   (b) biometric verification means positioned on the interactive medical card wherein the biometric verification means is in electrical communication with at least one processor configured for validating a biometric sample with a biometric identifier stored thereon; and (c) at least one sensor in electronic communication with the at least one processor equipped with computer executable instructions, wherein the at least one sensor is programmed for determining the interactive medical card is within a predetermined proximity to a client server computer enabled with an application program, and for releasing a detachable prescription element when the biometric sample is valid and the interactive medical card is within the predetermined proximity.

2. The apparatus of claim 1, wherein the detachable prescription element includes at least one flash memory card.

3. The apparatus of claim 1, wherein the biometric verification means includes but is not limited to: fingerprint recognition means, hand geometry recognition means, palm geometry recognition means, iris recognition means, retina recognition means, speech recognition means.

4. The apparatus of claim 3, wherein the fingerprint recognition means includes a fingerprint scanner.

5. The apparatus of claim 1, wherein medical information includes but is not limited to a patients: name, birthday, social security number, address, prescription date, prescribing physician registration number, prescription history, prescribing physician's electronic signature, date prescription filled, pharmacy's registration number, pharmacist's license number, age, blood type, sex, race, marital status, allergies, known medical conditions, family history, a treating physician's contact information, color of eyes, height, primary care physician's name, primary care physician's address, primary care physician's contact information, insurance provider's name, insurer's address, insurer's telephone number, medical history.

6. The apparatus of claim 1, wherein the at least one processor positioned is configured for performing any one or more of the following: validating a biometric sample with a biometric identifier stored thereon; releasing the detachable prescription element; and communicating with a computer via an application program.

7. The apparatus of claim 1, wherein the interactive medical card comprises of at least one memory means for storing a biometric identifier or patient medical information.

8. A system comprising:
(a) a client server computer enabled with an application program comprising of computer executable instructions;
(b) an interactive medical card that is an electronic data card configured for storing thereon a patient's medical information thereon;
(c) biometric verification means positioned on the interactive medical card wherein the biometric verification means is in electrical communication with at least one processor configured for validating a biometric sample with a biometric identifier stored thereon; and
(d) at least one sensor in electronic communication with the at least one processor equipped with computer executable instructions, wherein the at least one sensor is programmed for determining the interactive medical card is within a predetermined proximity to a client server computer enabled with an application program, and for releasing a detachable prescription element when the biometric sample is valid and the interactive medical card is within the predetermined proximity.

9. The system of claim 8, wherein the detachable prescription element includes at least one flash memory card.

10. The system of claim 8, wherein the biometric verification means is configured for receiving at least one biometric sample.

11. The system of claim 8, wherein the biometric verification means includes but is not limited to: fingerprint recognition means, hand geometry recognition means, palm geometry recognition means, iris recognition means, retina recognition means, speech recognition means.

12. The system of claim 11, wherein the fingerprint recognition means includes a fingerprint scanner.

13. The system of claim 8, wherein medical information includes but is not limited to name, birthday, social security number, address, prescription date, prescribing physician registration number, prescription history, prescribing physician's electronic signature, date prescription filled, pharmacy's registration number, pharmacist's license number, age, blood type, sex, race, marital status, allergies, known medical conditions, family history, a treating physician's contact information, color of eyes, height, primary care physician's name, primary care physician's address, primary care physician's contact information, insurance provider's name, insurer's address, insurer's telephone number, medical history.

14. The system of claim 8, wherein the interactive medical card includes at least one processor configured for performing any one or more of the following: validating a biometric sample with a biometric identifier stored thereon; releasing the detachable prescription element; and communicating with the computer via an application program.

15. The system of claim 8, further comprising the application program configured for performing any one or more of the following:
(i) establishing access to the patient's medical information stored on an interactive medical card;
(ii) retrieving patient's medical information from the interactive medical card;
(iii) storing patient's medical information received from a medical care provider on the interactive medical card; or the computer, or a combination of the computer and the interactive medical card;
(iv) validating authorized access to the patient's medical information by the medical care provider;
(v) detecting a presence of at least one medical information field, or fields, adapted for receiving patient medical information; and
(vi) automatically propagating the field or fields with patients medical information.

16. A method comprising of:
(a) receiving a biometric sample on an interactive medical card;
(b) comparing, using a processor, the biometric sample with the biometric identifier stored thereon with biometric verification means positioned on the interactive medical card;
(c) determining, using the processor, the biometric sample is a valid;
(d) verifying, using the processor, that the interactive medical card is within a predetermined proximity to a client's server computer enabled with an application program; and
(e) releasing a detachable prescription element housed within the interactive medical card when the biometric sample is valid and the interactive medical card is within the predetermined proximity.

17. The method of claim 16, wherein the detachable prescription element includes at least one flash memory card.

18. The method of claim 17, wherein the biometric verification means includes but is not limited to: fingerprint recognition means, hand geometry recognition means, palm geometry recognition means, iris recognition means, retina recognition means, speech recognition means.

19. The method of claim 17, wherein the fingerprint recognition means includes a fingerprint scanner.

20. The method of claim 16, wherein medical information includes but is not limited to name, birthday, social security number, address, prescription date, prescribing physician registration number, prescription history, prescribing physician's electronic signature, date prescription filled, pharmacy's registration number, pharmacist's license number, age, blood type, sex, race, marital status, allergies, known medical conditions, family history, a treating physician's contact information, color of eyes, height, primary care physician's name, primary care physician's address, primary care physician's contact information, insurance provider's name, insurer's address, insurer's telephone number, medical history.

21. The method of claim 16, further comprising:
   (a) releasing the detachable prescription element; and
   (b) communicating with a computer via an application program.

22. The method of claim 16, comprising reading any one or more of the following: a biometric sample, biometric identifier stored on the interactive medical card or medical information; releasing the detachable prescription element; and communicating with a computer via an application program.

\* \* \* \* \*